(12) United States Patent
Schubert et al.

(10) Patent No.: US 8,530,717 B2
(45) Date of Patent: Sep. 10, 2013

(54) PROCESS FOR THE INDUSTRIAL ISOLATION OF PROPENE

(75) Inventors: Markus Schubert, Ludwigshafen (DE); Ingo Richter, Schwetzingen (DE); Ulrich Mueller, Neustadt (DE); Frank Poplow, Overath (DE); William Dolan, Yardley, PA (US); Christoph Kiener, Weisenheim am Sand (DE)

(73) Assignee: BASF SE, Ludwigshafen (DE)

( * ) Notice: Subject to any disclaimer, the term of this patent is extended or adjusted under 35 U.S.C. 154(b) by 269 days.

(21) Appl. No.: 13/003,839

(22) PCT Filed: Jul. 17, 2009

(86) PCT No.: PCT/EP2009/059252
§ 371 (c)(1), (2), (4) Date: Jan. 12, 2011

(87) PCT Pub. No.: WO2010/010050
PCT Pub. Date: Jan. 28, 2010

(65) Prior Publication Data
US 2011/0118526 A1    May 19, 2011

(30) Foreign Application Priority Data
Jul. 21, 2008 (EP) ..................................... 08160796

(51) Int. Cl.
*C07C 7/12* (2006.01)

(52) U.S. Cl.
USPC .................. 585/830; 585/820; 95/90; 95/143; 502/401

(58) Field of Classification Search
None
See application file for complete search history.

(56) References Cited

U.S. PATENT DOCUMENTS

| | | | |
|---|---|---|---|
| 3,798,283 A | 3/1974 | Bitar et al. | |
| 3,862,256 A | 1/1975 | Isailingold et al. | |
| 3,887,631 A | 6/1975 | Yaffe | |
| 4,250,346 A | 2/1981 | Young et al. | |

(Continued)

FOREIGN PATENT DOCUMENTS

| CN | 1073893 | 7/1993 |
|---|---|---|
| CN | 1105352 | 7/1995 |

(Continued)

OTHER PUBLICATIONS

Li et al., Royal Society of Chemistry. Selective Gas Adsorption and Separation in Metal-Organic Frameworks, 2008. see abstract, p. 1478.*

(Continued)

*Primary Examiner* — In Suk Bullock
*Assistant Examiner* — Jelitza Perez
(74) *Attorney, Agent, or Firm* — Oblon, Spivak, McClelland, Maier & Neustadt, L.L.P.

(57) ABSTRACT

A process for the industrial isolation of propene from a gas stream comprising at least propene and propane, which involves contacting of the gas stream with an adsorbent having a porous metal organic framework having at least one at least bidentate organic compound coordinated to at least one metal ion, with the adsorbent becoming laden with propane and the gas stream therefore having an increased proportion of propene, wherein the W least bidentate organic compound is an imidazolate which is unsubstituted or has one or more substituents selected independently from of halogen, $C_{1-6}$-alkyl, phenyl, $NH_2$, $NH(C_{1-6}$-alkyl), $N(C_{1-6}$-alkyl)$_2$, OH, O-phenyl and O—$C_{1-6}$-alkyl.

20 Claims, 2 Drawing Sheets

(56) References Cited

U.S. PATENT DOCUMENTS

Figure 1:
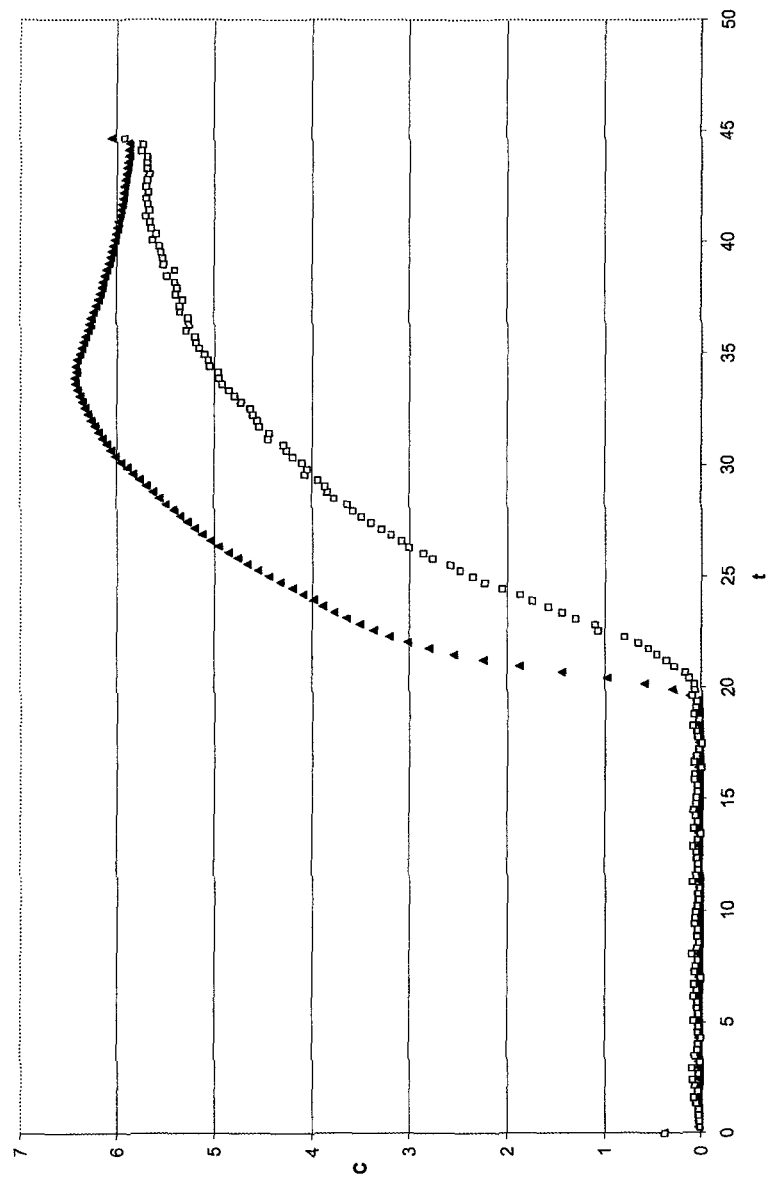

| | | | |
|---|---|---|---|
| 4,255,284 | A | 3/1981 | Hardman |
| 4,341,664 | A | 7/1982 | Antos |
| 4,788,371 | A | 11/1988 | Imai et al. |
| 5,086,032 | A | 2/1992 | Mazzocchia et al. |
| 5,220,091 | A | 6/1993 | Brinkmeyer et al. |
| 5,430,220 | A | 7/1995 | Khare et al. |
| 5,817,596 | A | 10/1998 | Akporiaye et al. |
| 5,877,369 | A | 3/1999 | Wu et al. |
| 5,922,925 | A | 7/1999 | Akporiaye et al. |
| 6,313,063 | B1 | 11/2001 | Rytter et al. |
| 7,556,673 | B2 | 7/2009 | Schubert et al. |
| 2009/0306420 | A1 | 12/2009 | Schubert et al. |
| 2009/0312591 | A1* | 12/2009 | Schubert et al. ............... 585/654 |
| 2010/0029476 | A1 | 2/2010 | Trukhan et al. |
| 2010/0056836 | A1 | 3/2010 | Mueller et al. |
| 2010/0064888 | A1 | 3/2010 | Schubert et al. |
| 2010/0076220 | A1 | 3/2010 | Schubert et al. |
| 2010/0126344 | A1 | 5/2010 | Stein et al. |
| 2010/0133280 | A1 | 6/2010 | Stein et al. |
| 2010/0154635 | A1 | 6/2010 | Schubert et al. |
| 2010/0178767 | A1 | 7/2010 | Schubert et al. |
| 2010/0197990 | A1 | 8/2010 | Schubert et al. |

FOREIGN PATENT DOCUMENTS

| | | |
|---|---|---|
| DE | 195 30 454 | 2/1997 |
| DE | 196 22 331 | 12/1997 |
| DE | 198 35 247 | 2/1999 |
| DE | 197 53 817 | 6/1999 |
| DE | 199 37 105 | 2/2001 |
| DE | 199 37 106 | 2/2001 |
| DE | 199 37 107 | 2/2001 |
| DE | 100 28 582 | 12/2001 |
| DE | 100 51 419 | 4/2002 |
| DE | 101 19 933 | 10/2002 |
| DE | 102 11 275 | 9/2003 |
| EP | 0 117 146 | 8/1984 |
| EP | 0 294 845 | 12/1988 |
| EP | 0 318 295 | 5/1989 |
| EP | 0 529 853 | 3/1993 |
| EP | 0 603 838 | 6/1994 |
| EP | 0 608 836 | 8/1994 |
| EP | 0 608 838 | 8/1994 |
| EP | 0 700 714 | 3/1996 |
| EP | 0 700 893 | 3/1996 |
| EP | 0 705 136 | 4/1996 |
| EP | 0 895 809 | 2/1999 |
| EP | 0 962 253 | 12/1999 |
| EP | 1 192 987 | 4/2002 |
| WO | 97 36849 | 10/1997 |
| WO | 99 29420 | 6/1999 |
| WO | 99 46039 | 9/1999 |
| WO | 00 48971 | 8/2000 |
| WO | 03 102000 | 12/2003 |
| WO | 2007 113085 | 10/2007 |
| WO | 2007 113118 | 10/2007 |
| WO | 2007 131955 | 11/2007 |
| WO | 2008 062034 | 5/2008 |
| WO | 2008 129024 | 10/2008 |
| WO | 2009 092494 | 7/2009 |

OTHER PUBLICATIONS

Li et al., Journal of American Chemical Society. Zeolitic Imidazolate Frameworks for Kinetic Separation of Propane and Propene. 2009, p. 10368-10369.*

Da Silva, F. A. et al., "Vacuum Swing Adsorption for Propylene/Propane Separation with 4A Zeolite", Ind. Eng. Chem. Res., vol. 40, No. 24, pp. 5758-5774, (Nov. 3, 2001).

U.S. Appl. No. 12/521,337, filed Jun. 26, 2009, Schubert, et al.
U.S. Appl. No. 12/863,339, filed Jul. 16, 2010, Schubert, et al.
U.S. Appl. No. 12/921,505, filed Sep. 8, 2010, Leung, et al.
U.S. Appl. No. 13/003,230, filed Jan. 7, 2011, Richter, et al.

Da Silva, F. A. et al., "Vacuum Swing Adsorption for Propylene/Propane Separation with 4A Zeolite", Ind. Eng. Chem. Res., vol. 40, No. 24, pp. 5758-5774, (Nov. 3, 2001).

Da Silva, F. A. et al., "Propylene/Propane Separation by Vacuum Swing Adsorption Using 13X Zeolite", AICHE Journal, vol. 47, No. 2, pp. 341-357, (Feb. 2001).

Grande, C. A. et al., "Propane/Propylene Separation by Pressure Swing Adsorption Using Zeolite 4A", Ind. Eng. Chem. Res., vol. 44, No. 23, pp. 8815-8829, (Oct. 15, 2005).

International Search Report issued Nov. 10, 2009 in PCT/EP09/059252 filed Jul. 17, 2009.

* cited by examiner

PROCESS FOR THE INDUSTRIAL ISOLATION OF PROPENE

The present invention relates to a process for the industrial isolation of propene from a gas stream comprising at least propene and propane and also the use of a porous metal organic framework for the enrichment of propene.

Propene is an important product of value which serves, for example, as starting material for the preparation of polypropene.

Propene and its homologous olefins occurs in only very small amounts in natural gas or petroleum. Its direct isolation from natural sources is therefore not of economic importance.

However, there are many industrial processes in which a mixture of, in particular, propane and propene is formed, for example propane dehydrogenation, FCC or steam cracking, MTO (methanol to olefin), etc. In all these processes, it is therefore necessary to separate off the propene from the hydrocarbon product mixture. This also applies to the preparation of propene by olefin metathesis. If appropriate, a number of purification steps have to precede this separation.

One possible separation method is distillation, but because of, in particular, the similar boiling points of propane and propene (according to VDI-Wärmeatlas, 5.7 K at 1 bar; 6.1 K at 5 bar) and the high purity requirements which the propene has to meet, this requires a large number of theoretical plates and is correspondingly complicated and expensive.

A method of separating off and isolating propene which is superior to distillation is adsorption.

Classical adsorbents for the industrial isolation of propene from gas mixtures comprising propene together with further hydrocarbons, in particular propane, are zeolites.

Such zeolite-based processes are described by F. A. Da Silva et al., Int. Eng. Chem. Res. 40 (2001), 5758-5774; F. A. Da Silva et al., AIChE Journal 47 (2001), 341-357 and C. A. Grande et al., Int. Eng. Chem. Res. 44 (2005), 8815-8829.

WO-A 2007/113118 likewise describes a process for the industrial isolation of propene by means of metal organic frameworks, but here propene is, as customary, removed from the gas stream by adsorption.

Despite the processes for the industrial isolation of propene which are known from the prior art, there continues to be a need for alternative processes.

It is therefore an object of the present invention to provide such processes.

The object is achieved by a process for the industrial isolation of propene from a gas stream comprising at least propene and propane, which comprises the step contacting of the gas stream with an adsorbent comprising a porous metal organic framework comprising at least one at least bidentate organic compound coordinated to at least one metal ion, with the adsorbent becoming laden with propane and the gas stream therefore having an increased proportion of propene, wherein the at least bidentate organic compound is an imidazolate which is unsubstituted or has one or more substituents selected independently from the group consisting of halogen, $C_{1-6}$-alkyl, phenyl, $NH_2$, $NH(C_{1-6}$-alkyl), $N(C_{1-6}$-alkyl)$_2$, OH, O-phenyl and O—$C_{1-6}$-alkyl.

It has been found that, in contrast to the conventional adsorption behavior which is known from metal organic frameworks in general and zeolites, the specific imidazolate-based porous metal organic framework preferentially adsorbs propane, so that a gas stream which comprises propene together with at least propane and, after contacting with an adsorbent comprising the specific metal organic framework, is enriched in propane is obtained. This has the advantage that the product of value remains in the gas stream and subsequent desorption is therefore not necessary. Desorption is normally disadvantageous since the pressure usually has to be lowered so that a propene-rich fraction usually has to be decompressed before further processing, which involves a considerable energy consumption. In addition, in separations using the pressure-swing and/or temperature-swing principle, it is often difficult to isolate the absorbed components in high purity in the desorption phase, since it is not possible to completely prevent the proportion of the intergrain volume which has not been separated off from getting into the product.

The proportion of propene in the gas stream can have various values, with this proportion depending greatly on the source of the gas stream. However, the proportion of propane based on the sum of the proportions by volume of propene and propane which is present in the gas stream is particularly important since this separation represents the main problem. The removal of other constituents of the gas stream can, if appropriate, occur in a preceding step and can also be effected by means of other adsorbents instead of a porous metal organic framework. Furthermore, other methods such as distillation can also be used for this purpose.

In addition to propene, the gas stream comprises at least propane. A plurality of further hydrocarbons can typically be comprised in addition.

Preference is given to the gas stream comprising from 20 to 80% by volume of propene, based on the sum of the proportions by volume of propene and the further hydrocarbon or further hydrocarbons in the gas stream.

The proportion of propene is more preferably from 30 to 70% by volume. It is also preferred that the absolute content of propene in the gas stream can have these values.

In a preferred embodiment, the gas stream is an optionally purified product stream from the preparation of propene.

Such product streams typically comprise, in addition to propene, further homologous alkanes, in particular propane, and alkenes and also further gaseous constituents which, however, can be removed by simple purification steps. An example of such a constituent of a product stream from propene production which can be removed by purification is gaseous water which can be removed appropriately by means of a conventional desiccant or by condensation during compression and cooling. A further example is carbon dioxide which can be removed by means of a simple gas scrub. Further examples are ethyne and allenes which can be selectively hydrogenated beforehand.

As an alternative to cracking processes, an olefin metathesis can also be used for propene production. Here, ethene and 2-butene can be reacted to form propene.

Finally, the transformation of methanol or dimethyl ether is also a more or less specific method of preparing propene. Such reactions are also referred to as "methanol to olefins". These reactions over zeolites (ZSM-5 or SAPO) are aimed at either a preparation of propene/ethene together with traces of $C_5^+$ or a preparation of propene/gasoline. In both cases, propene has to be separated off from, inter alia, more or less large amounts of LPG.

A particularly preferred preparation of propene for producing an optionally purified product stream is dehydrogenation of propane.

In a preferred embodiment of the present invention, the optionally purified product stream therefore originates from a cracking process, a dehydrogenation of propane, an olefin metathesis or a methanol transformation for the preparation of propene, in particular from a dehydrogenation of propane.

It is likewise possible for appropriate mixtures of such different product streams to be used.

A preferred process for the dehydrogenation of propane comprises the steps:
A) a propane-comprising feed gas stream a is provided;
B) the propane-comprising feed gas stream a, if appropriate water vapor and if appropriate an oxygen-comprising gas stream are fed into a dehydrogenation zone and propane is subjected to dehydrogenation to propene, giving a product gas stream b comprising propane, propene, methane, ethane, ethene, hydrogen, possibly carbon monoxide, carbon dioxide, water vapor and oxygen;
C) the product gas stream b is cooled, if appropriate compressed and water vapor is separated off by condensation, giving a product gas stream c depleted in water vapor.

In a first part A) of the process, a propane-comprising feed gas stream a is provided. This generally comprises at least 80% by volume of propane, preferably 90% by volume of propane. In addition, the propane-comprising feed gas stream a generally further comprises butanes (n-butane, isobutane). Typical compositions of the propane-comprising feed gas stream are disclosed in DE-A 102 46 119 and DE-A 102 45 585. The propane-comprising feed gas stream a is usually obtained from liquid petroleum gas (LPG).

In a part B) of the process, the propane-comprising feed gas stream is fed into a dehydrogenation zone and subjected to a generally catalytic dehydrogenation. Here, propane is partly dehydrogenated to propene over a dehydrogenation-active catalyst in a dehydrogenation reactor. In addition, hydrogen and small amounts of methane, ethane, ethene and $C_4^+$-hydrocarbons (n-butane, isobutane, butenes, butadiene) are formed. In general, carbon oxides (CO, $CO_2$), in particular $CO_2$, water vapor and possibly small amounts of inert gases are also obtained in the product gas mixture of the catalytic propane dehydrogenation. The product gas stream from the dehydrogenation generally comprises water vapor which is added to the dehydrogenation gas mixture and/or, in the case of dehydrogenation in the presence of oxygen (oxidative or nonoxidative), is formed in the dehydrogenation. Inert gases (nitrogen) are introduced into the dehydrogenation zone together with the oxygen-comprising gas stream fed in when the dehydrogenation is carried out in the presence of oxygen, unless pure oxygen is fed in. If an oxygen-comprising gas is fed in, its oxygen content is generally at least 40% by volume, preferably at least 80% by volume, particularly preferably at least 90% by volume, in particular technical-grade oxygen having an oxygen content of >99%, in order to avoid an excessively high proportion of inert gas in the product gas mixture. In addition, unreacted propane is present in the product gas mixture.

The dehydrogenation of propane can in principle be carried out in all types of reactor known from the prior art. A comparatively comprehensive description of reactor types which are suitable for the purpose of the invention is also given in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

The dehydrogenation can be carried out as an oxidative or nonoxidative dehydrogenation. The dehydrogenation can be carried out isothermally or adiabatically. The dehydrogenation can be carried out catalytically in a fixed-bed, moving-bed or fluidized-bed reactor.

The oxidative catalytic dehydrogenation of propane is preferably carried out autothermally. To achieve this, additional oxygen is mixed into the reaction gas mixture for the propane dehydrogenation in at least one reaction zone and the hydrogen and/or hydrocarbon comprised in the reaction gas mixture is at least partly burnt, resulting in at least part of the heat of dehydrogenation required being generated directly in the reaction gas mixture in the at least one reaction zone.

A feature of the nonoxidative mode of operation compared to an oxidative mode of operation is the at least intermediate formation of hydrogen which shows up in the presence of hydrogen in the product gas from the dehydrogenation. In the case of oxidative dehydrogenation, no free hydrogen is present in the product gas from the dehydrogenation.

A suitable reactor shape is the fixed-bed tube or shell-and-tube reactor. In these, the catalyst (dehydrogenation catalyst and, if appropriate, specific oxidation catalyst) is present as a fixed bed in a reaction tube or in a bundle of reaction tubes. Customary internal diameters of the reaction tube(s) are from about 10 to 15 cm. A typical shell-and-tube dehydrogenation reactor comprises from about 300 to 1000 reaction tubes. The temperature in the interior of the reaction tube(s) is usually in the range from 300 to 1200° C., preferably in the range from 500 to 1000° C. The working pressure is usually in the range from 0.5 to 8 bar, frequently in the range from 1 to 2 bar, when using a low steam dilution but also in the range from 3 to 8 bar when using a high steam dilution (corresponding to the "steam active reforming process" (STAR process) or the Linde process) for the dehydrogenation of propane or butane of Phillips Petroleum Co. Typical space velocities of the catalyst (GHSVs) are in the range from 500 to 2000 $h^{-1}$, based on hydrocarbon used. The catalyst geometry can be, for example, spherical or cylindrical (hollow or solid).

The catalytic dehydrogenation of propane can also be carried out over a heterogeneous catalyst in a fluidized bed, corresponding to the Snamprogetti/Yarsintez-FBD process. Here, two fluidized beds are advantageously operated side by side, with one generally being in the state of regeneration. The working pressure is typically from 1 to 2 bar, and the dehydrogenation temperature is generally from 550 to 600° C. The heat required for the dehydrogenation can be introduced into the reaction system by preheating the dehydrogenation catalyst to the reaction temperature. The preheaters can be partly dispensed with by introduction of an oxygen-comprising cofeed, with the required heat being generated directly in the reactor system by combustion of hydrogen and/or hydrocarbons in the presence of oxygen. If appropriate, a hydrogen-comprising cofeed can additionally be mixed in.

The catalytic dehydrogenation of propane can be carried out in a tray reactor. If the dehydrogenation is carried out autothermally with introduction of an oxygen-comprising gas stream, it is preferably carried out in a tray reactor. This comprises one or more successive catalyst beds. The number of catalyst beds can be from 1 to 20, advantageously from 1 to 6, preferably from 1 to 4 and in particular from 1 to 3. The reaction gas preferably flows radially or axially through the catalyst beds. In general, such a tray reactor is operated using one fixed bed of catalyst. In the simplest case, the fixed beds of catalyst are arranged axially in a shaft furnace reactor or in the annular gaps of concentrically arranged cylindrical gratings. A shaft furnace reactor corresponds to one tray. Carrying out the dehydrogenation in a single shaft furnace reactor corresponds to one embodiment. In a further preferred embodiment, the dehydrogenation is carried out in a tray reactor having 3 catalyst beds.

In general, the amount of the oxygen-comprising gas added to the reaction mixture is selected so that the combustion of hydrogen present in the reaction gas mixture and, if appropriate, of hydrocarbons present in the reaction gas mixture and/or of carbon present in the form of carbonaceous deposits generates the quantity of heat required for the dehydrogenation of the propane. In general, the total amount of oxygen fed in, based on the total amount of propane, is from 0.001 to 0.8 mol/mol, preferably from 0.001 to 0.6 mol/mol, particularly preferably from 0.02 to 0.5 mol/mol. Oxygen can be used either as pure oxygen or as oxygen-comprising gas which comprises inert gases. However, to avoid high propane and propene losses in the work-up (see below), it is important that the oxygen content of the oxygen-comprising gas used is high and is at least 40% by volume, preferably at least 80% by volume, particularly preferably at least 90% by volume. A particularly preferred oxygen-comprising gas is technical-grade oxygen having an $O_2$ content of about 99% by volume.

The hydrogen burnt to generate heat is the hydrogen formed in the catalytic dehydrogenation of propane and also any additional hydrogen added as hydrogen-comprising gas to the reaction gas mixture. There is preferably such an amount of hydrogen present that the molar ratio of $H_2/O_2$ in the reaction gas mixture immediately before the introduction of oxygen is from 1 to 10 mol/mol, preferably from 2 to 5 mol/mol. In the case of multistage reactors, this applies for each intermediate introduction of oxygen-comprising and, if appropriate, hydrogen-comprising gas.

The combustion of hydrogen occurs catalytically. The dehydrogenation catalyst used generally also catalyzes the combustion of hydrocarbons and of hydrogen by means of oxygen, so that in principle no specific oxidation catalyst different from this is necessary. In one embodiment, the dehydrogenation is carried out in the presence of one or more oxidation catalysts which selectively catalyze the combustion of hydrogen by means of oxygen in the presence of hydrocarbons. As a result, the combustion of these hydrocarbons by means of oxygen to form CO, $CO_2$ and water proceeds only to a minor extent. The dehydrogenation catalyst and the oxidation catalyst are preferably present in different reaction zones.

In the case of multistage reaction, the oxidation catalyst can be present in only one reaction zone, in a plurality of reaction zones or in all reaction zones.

The catalyst which selectively catalyzes the oxidation of hydrogen is preferably arranged at the places where higher oxygen partial pressures prevail than at other places in the reactor, in particular in the vicinity of the point at which the oxygen-comprising gas is fed in. Oxygen-comprising gas and/or hydrogen-comprising gas can be fed in at one or more places on the reactor.

In an embodiment of the process of the invention, an intermediate introduction of oxygen-comprising gas and of hydrogen-comprising gas is carried out before each tray of a tray reactor. In a further embodiment of the process of the invention, the introduction of oxygen-comprising gas and of hydrogen-comprising gas is carried out before each tray apart from the first tray. In one embodiment, a layer of a specific oxidation catalyst is present downstream of each point or introduction, followed by a layer of the dehydrogenation catalyst. In a further embodiment, no specific oxidation catalyst is present. The dehydrogenation temperature is generally from 400 to 1100° C., and the pressure in the last catalyst bed of the tray reactor is generally from 0.2 to 15 bar, preferably from 1 to 10 bar, particularly preferably from 1 to 5 bar. The space velocity (GHSV) is generally from 500 to 2000 $h^{-1}$; in high-load operation, it can also be up to 100 000 $h^{-1}$, preferably from 4000 to 16 000 $h^{-1}$.

A preferred catalyst which selectively catalyzes the combustion of hydrogen comprises oxides and/or phosphates selected from the group consisting of the oxides and phosphates of germanium, tin, lead, arsenic, antimony or bismuth.

A further preferred catalyst which catalyzes the combustion of hydrogen comprises a noble metal of transition group(s) VIII and/or I.

The dehydrogenation catalysts used generally comprise a support and an active composition. The support generally comprises a heat-resistant oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof as supports. The mixtures can be physical mixtures or chemical mixed phases such as mixed magnesium- or zinc-aluminum oxides. Preferred supports are zirconium dioxide and/or silicon dioxide, particularly preferably mixtures of zirconium dioxide and silicon dioxide.

Suitable shaped catalyst body geometries are rods, stars, rings, saddles, spheres, foams and monoliths having characteristic dimensions of from 1 to 100 mm.

The active composition of the dehydrogenation catalysts generally comprises one or more elements of transition group VIII, preferably platinum and/or palladium, particularly preferably platinum. In addition, the dehydrogenation catalysts can comprise one or more elements of main groups I and/or II, preferably potassium and/or cesium. Furthermore, the dehydrogenation catalysts can comprise one or more elements of transition group III including the lanthanides and actinides, preferably lanthanum and/or cerium. Finally, the dehydrogenation catalysts can comprise one or more elements of main groups III and/or IV, preferably one or more elements from the group consisting of boron, gallium, silicon, germanium, tin and lead, particularly preferably tin.

In a preferred embodiment, the dehydrogenation catalyst comprises at least one element of transition group VIII, at least one element of main groups I and/or II, at least one element of main groups III and/or IV and at least one element of transition group III including the lanthanides and actinides.

For the purposes of the invention, it is possible to use, for example, all dehydrogenation catalysts disclosed in WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, EP 0 117 146, DE-A 199 37 106, DE-A 199 37 105 and DE-A 199 37 107. Particularly preferred catalysts for the above-described variants of the autothermal dehydrogenation of propane are the catalysts described in examples 1, 2, 3 and 4 of DE-A 199 37 107.

The autothermal dehydrogenation of propane is preferably carried out in the presence of water vapor. The water vapor added serves as heat carrier and aids the gasification of organic deposits on the catalysts, as a result of which the carbonization of the catalysts is countered and the operating life of the catalysts is increased. The organic deposits are in this case converted into carbon monoxide, carbon dioxide and possibly water. Dilution with water vapor increases the equilibrium conversion.

The dehydrogenation catalyst can be regenerated in a manner known per se. Thus, water vapor can be added to the reaction gas mixture or an oxygen-comprising gas can from time to time be passed over the catalyst bed at elevated temperature so that the deposited carbon is burnt off. If appropriate, the catalyst is reduced by means of a hydrogen-comprising gas after regeneration.

The product gas stream b can be divided into two substreams, with one substream being recirculated to the autothermal dehydrogenation, corresponding to the gas recycle process described in DE-A 102 11 275 and DE-A 100 28 582.

The dehydrogenation of propane can also be carried out as an oxidative dehydrogenation. The oxidative dehydrogenation of propane can be carried out as a homogeneous oxidative dehydrogenation or as a heterogeneously catalyzed oxidative dehydrogenation.

If the dehydrogenation of propane is configured as a homogeneous oxydehydrogenation in the process of the invention, this can in principle be carried out as described in U.S. Pat. No. 3,798,283, CN-A 1,105,352, Applied Catalysis, 70 (2), 1991, pp. 175 to 187, Catalysis Today 13, 1992, pp. 673 to 678, and the earlier patent application DE-A 1 96 22 331.

The temperature of the homogeneous oxydehydrogenation is generally in the range from 300 to 700° C., preferably from 400 to 600° C., particularly preferably from 400 to 500° C. The pressure can be from 0.5 to 100 bar or from 1 to 50 bar. It will frequently be from 1 to 20 bar, in particular from 1 to 10 bar.

The residence time of the reaction gas mixture under oxydehydrogenation conditions is usually from 0.1 or 0.5 to 20 sec, preferably from 0.1 or 0.5 to 5 sec. As reactor, it is possible to use, for example, a tube furnace or a shell-and-tube reactor, e.g. a countercurrent tube furnace using flue gas as heat transfer medium or a shell-and-tube reactor using a salt melt as heat transfer medium.

The propane to oxygen ratio in the starting mixture used can be from 0.5:1 to 40:1. The molar ratio of propane to molecular oxygen in the starting mixture is preferably $\leq 6:1$, more preferably $\leq 5:1$. In general, the abovementioned ratio will be $\geq 1:1$, for example $\geq 2:1$. The starting mixture can comprise further, essentially inert constituents such as $H_2O$, $CO_2$, CO, $N_2$, noble gases and/or propene. Propene can be comprised in the $C_3$ fraction coming from the refinery. It is advantageous in a homogeneous oxidative dehydrogenation of propane to propene for the ratio of the surface area of the reaction space to the volume of the reaction space to be as small as possible, since the homogeneous oxidative dehydrogenation of propane proceeds by a free-radical mechanism and the surface of the reaction space generally acts as free-radical scavenger. Particularly advantageous surface materials are aluminum oxides, fused silica, borosilicates, stainless steel and aluminum.

If the first reaction stage in the process of the invention is configured as a heterogeneously catalyzed oxydehydrogenation, this can in principle be carried out as described in U.S. Pat. No. 4,788,371, CN-A 1,073,893, Catalysis Letters 23 (1994) 103-106, W. Zhang, Gaodeng Xuexiao Huaxue Xuebao, 14 (1993)566, Z. Huang, Shiyou Huagong, 21 (1992) 592, WO 97/36849, DE-A 1 97 53 817, U.S. Pat. No. 3,862,256, U.S. Pat. No. 3,887,631, DE-A 1 95 30 454, U.S. Pat. No. 4,341,664, J. of Catalysis 167, 560-569 (1997), J. of Catalysis 167, 550-559 (1997), Topics in Catalysis 3 (1996) 265-275, U.S. Pat. No. 5,086,032, Catalysis Letters 10 (1991) 181-192, Ind. Eng. Chem. Res. 1996, 35, 14-18, U.S. Pat. No. 4,255,284, Applied Catalysis A: General, 100 (1993) 111-130, J. of Catalysis 148, 56-67 (1994), V. Cortés Corberén and S. Vic Bellón (Editors), New Developments in Selective Oxidation II, 1994, Elsevier Science B.V., pp. 305-313, 3rd World Congress on Oxidation Catalysis R. K. Grasselli, S. T. Oyama, A. M. Gaffney and J. E. Lyons (Editors), 1997, Elsevier Science B.V., pp. 375 ff. In particular, all oxydehydrogenation catalysts mentioned in the abovementioned documents can be used. What has been said in relation to the abovementioned documents also applies to:

i) Otsuka, K.; Uragami, Y.; Komatsu, T.; Hatano, M. in Natural Gas Conversion, Stud. Surf. Sci. Catal.; Holmen A.; Jens, K.-J.; Kolboe, S., Eds.; Elsevier Science: Amsterdam, 1991; Vol. 61, p 15;
ii) Seshan, K.; Swaan, H. M.; Smits, R. H. H.; van Ommen, J. G.; Ross, J. R. H. in New Developments in Selective Oxidation; Stud. Surf. Sci. Catal.; Centi, G.; Trifirò, F., Eds.; Elsevier Science: Amsterdam 1990; Vol. 55, p 505;
iii) Smits, R. H. H.; Seshan, K.; Ross, J. R. H. in New Developments in Selective Oxidation by Heterogeneous Catalysis; Stud. Surf. Sci. Catal.; Ruiz, P.; Delmon, B., Eds.; Elsevier Science Amsterdam, 1992 a; Vol. 72, p 221;
iv) Smits, R. H. H.; Seshan, K.; Ross, J. R. H. Proceedings, Symposium on Catalytic Selective Oxidation, Washington D.C.; American Chemical Society: Washington, D.C., 1992 b; 1121;
v) Mazzocchia, C.; Aboumrad, C.; Daigne, C.; Tempesti, E.; Herrmann, J. M.; Thomas, G. Catal. Lett. 1991, 10, 181;
vi) Bellusi, G.; Conti, G.; Perathonar, S.; Trifirò, F. Proceedings, Symposium on Catalytic Selective Oxidation, Washington, D.C.; American Chemical Society: Washington, D.C., 1992; p 1242;
vii) Ind. Eng. Chem. Res. 1996, 35, 2137-2143 and
viii) Symposium on Heterogeneons Hydrocarbon Oxidation Presented before the Division of Petroleum Chemistry, Inc. 211th National Meeting, American Chemical Society New Orleans, La., Mar. 24-29, 1996.

Particularly suitable oxydehydrogenation catalysts are the multimetal oxide compositions or catalysts A of DE-A 1 97 53 817, with the multimetal oxide compositions or catalysts A mentioned as preferred being very particularly useful, i.e. possible active compositions are, in particular, multimetal oxide compositions of the general formula I $$M^1_a Mo_{1-b} M^2_b O_x \qquad (I),$$

where
M¹=Co, Ni, Mg, Zn, Mn and/or Cu,
M²=W, V, Te, Nb, P, Cr, Fe, Sb, Ce, Sn and/or La,
a=from 0.5 to 1.5,
b=from 0 to 0.5 and
x=a number which is determined by the valence and abundance of the elements other than oxygen in I.

Further multimetal oxide compositions suitable as oxydehydrogenation catalysts are mentioned below:

Suitable Mo—V—Te/Sb—Nb—O multimetal oxide catalysts are disclosed in EP-A 0 318 295, EP-A 0 529 853, EP-A 0 603 838, EP-A 0 608 836, EP-A 0 608 838, EP-A 0 895 809, EP-A 0 962 253, EP-A 1 192 987, DE-A 198 35 247, DE-A 100 51 419 and DE-A 101 19 933.

Suitable Mo—V—Nb—O multimetal oxide catalysts are described, inter alia, in E. M. Thorsteinson, T. P. Wilson, F. G. Young, P. H. Kasei, Journal of Catalysis 52 (1978), pages 116 to 132, and in U.S. Pat. No. 4,250,346 and EP-A 0 294 845.

Suitable Ni—X—O multimetal oxide catalysts in which X=Ti, Ta, Nb, Co, Hf, W, Y, Zn, Zr, Al are described in WO 00/48971.

In principle, suitable active compositions can be produced in a simple manner by producing a very intimate, preferably finely divided dry mixture having a composition corresponding to their stoichiometry from suitable sources of their components and calcining this at temperatures of from 450 to 1000° C. The calcination can be carried out either under inert gas or under an oxidizing atmosphere such as air (mixture of inert gas and oxygen) and also under a reducing atmosphere (e.g. mixture of inert gas, oxygen and $NH_3$, CO and/or $H_2$). Possible sources of the components of the multimetal oxide active compositions are oxides and/or compounds which can be converted into oxides by heating, at least in the presence of oxygen. Apart from the oxides, possible starting compounds are, in particular, halides, nitrates, formates, oxalates, citrates, acetates, carbonates, amine complexes, ammonium salts and/or hydroxides.

The multimetal oxide compositions can be used either in powder form or after shaping into particular catalyst geometries in the process of the invention, with shaping being able to be carried out before or after the subsequent calcination. Suitable all-active catalyst geometries are, for example, solid cylinders or hollow cylinders having an external diameter and a length of from 2 to 10 mm. In the case of hollow cylinders, a wall thickness of from 1 to 3 mm is advantageous. Suitable hollow cylinder geometries are, for example, 7 mm×7 mm×4 mm or 5 mm×3 mm×2 mm or 5 mm×2 mm×2 mm (in each case length×external diameter×internal diameter). Of course, the all-active catalyst can also have a spherical geometry, with the sphere diameter being able to be from 2 to 10 mm.

Of course, shaping of the pulverulent active composition or its pulverulent, not yet calcined, precursor composition can also be effected by application to preshaped inert catalyst supports. The layer thickness of the powder composition applied to the support bodies is advantageously in the range from 50 to 500 mm, preferably in the range from 150 to 250 mm. As support materials, it is possible to use customary porous or nonporous aluminum oxides, silicon dioxide, thorium dioxide, zirconium dioxide, silicon carbide or silicates such as magnesium or aluminum silicate. The support bodies can have a regular or irregular shape, with regularly shaped support bodies having a pronounced surface roughness, e.g. spheres, hollow cylinders or saddles having dimensions in the range from 1 to 100 mm, being preferred. The use of essentially nonporous, spherical steatite supports which have a rough surface and a diameter of from 1 to 8 mm, preferably from 4 to 5 mm, is appropriate.

The reaction temperature of the heterogeneously catalyzed oxydehydrogenation of propane is generally from 300 to 600° C., usually from 350 to 500° C. The pressure is from 0.2 to 15 bar, preferably from 1 to 10 bar, for example from 1 to 5 bar. Pressures above 1 bar, e.g. from 1.5 to 10 bar, have been found to be particularly advantageous. In general, the heterogeneously catalyzed oxydehydrogenation of propane is carried out over a fixed bed of catalyst. The latter is advantageously poured into the tubes of a shell-and-tube reactor, as described, for example, in EP-A 700 893 and EP-A 700 714 and also the references cited in these documents. The average residence time of the reaction gas mixture in the catalyst bed is normally from 0.5 to 20 seconds. The propane to oxygen ratio in the reaction gas starting mixture used for the heterogeneously catalyzed oxydehydrogenation of propane can, according to the invention, be from 0.5:1 to 40:1. It is advantageous for the molar ratio of propane to molecular oxygen in the starting gas mixture to be ≦6:1, preferably ≦5:1. The abovementioned ratio will generally be ≧1:1, for example 2:1. The starting gas mixture can comprise further, essentially inert constituents such as $H_2O$, $CO_2$, CO, $N_2$, noble gases and/or propene. In addition, a certain proportion of $C_1$-, $C_2$- and $C_4$-hydrocarbons can be comprised.

The product gas stream b leaving the dehydrogenation zone is generally under a pressure of from 0.2 to 15 bar, preferably from 1 to 10 bar, particularly preferably from 1 to 5 bar, and has a temperature in the range from 300 to 700° C.

The dehydrogenation of propane results in a gas mixture which generally has the following composition: from 10 to 80% by volume of propane, from 5 to 50% by volume of propene, from 0 to 20% by volume of methane, ethane, ethene and $C_4^+$-hydrocarbons, from 0 to 30% by volume of carbon oxides, from 0 to 70% by volume of water vapor and from 0 to 25% by volume of hydrogen and also from 0 to 50% by volume of inert gases.

The preferred autothermal dehydrogenation of propane gives a gas mixture which generally has the following composition: from 10 to 80% by volume of propane, from 5 to 50% by volume of propene, from 0 to 20% by volume of methane, ethane, ethene and $C_4^+$-hydrocarbons, from 0.1 to 30% by volume of carbon oxides, from 1 to 70% by volume of water vapor and from 0.1 to 25% by volume of hydrogen and also from 0 to 30% by volume of inert gases In part C) of the process, water is firstly separated off from the product gas stream b. The removal of water is carried out by condensation by cooling and, if appropriate, compression of the product gas stream b and can be carried out in one or more cooling and, if appropriate, compression stages. In general, the product gas stream b is for this purpose cooled to a temperature in the range from 20 to 80° C., preferably from 40 to 65° C. In addition, the product gas stream can be compressed, generally to a pressure in the range from 2 to 40 bar, preferably from 5 to 20 bar, particularly preferably from 10 to 20 bar.

In an embodiment of the process of the invention, the product gas stream b is passed through a cascade of heat exchangers and in this way firstly cooled to a temperature in the range from 50 to 200° C. and subsequently cooled further by means of water in a quenching tower to a temperature of from 40 to 80° C., for example 55° C. In this cooling procedure, the major part of the water vapor condenses out, but also part of the $C_4^+$-hydrocarbons comprised in the product gas stream b, in particular the $C_5^+$-hydrocarbons. Suitable heat exchangers are, for example, direct heat exchangers and countercurrent heat exchangers such as gas-gas countercurrent heat exchangers and also air coolers.

This gives a product gas stream c depleted in water vapor. This generally still comprises from 0 to 10% by volume of water vapor. To achieve virtually complete removal of water from the product gas stream c, it is possible, when using particular adsorbents in step D), to provide drying by means of molecular sieves, in particular 3A, 4A, 13X molecular sieves or aluminum oxides, or membranes.

Before carrying out step (a) of the process of the invention for the industrial isolation of propene, carbon dioxide can be separated off from the gas stream c by means of a gas scrub or by adsorption on solid adsorbents. The carbon dioxide gas scrub can be preceded by a separate combustion stage in which carbon monoxide is selectively oxidized to carbon dioxide.

To separate off $CO_2$, use is generally made of sodium hydroxide solution, potassium hydroxide solution or an alkanolamine solution as scrubbing liquid, with preference being given to using an activated N-methyldiethanolamine solution. In general, the product gas stream c is compressed to a pressure in the range from 5 to 25 bar by means of single-stage or multistage compression before carrying out the gas scrub. A stream c depleted in carbon dioxide and having a $CO_2$ content of generally <1000 ppm, preferably <100 ppm, particularly preferably <20 ppm, can be obtained.

However, preference is given to separating off $CO_2$ by sorption on suitable solid sorbents, for example molecular sieve 13X, calcium oxide, barium oxide, magnesium oxide or hydrotalcites.

In a particularly preferred embodiment, the purified product stream obtained in this way from the preparation of propene represents the gas stream comprising at least propane and propene which is used in the process of the invention for the industrial isolation of propene.

The adsorbent comprises a porous metal organic framework comprising at least one at least bidentate organic compound coordinated to at least one metal ion, wherein the at least bidentate organic compound is an imidazolate which is unsubstituted or has one or more substituents selected independently from the group consisting of halogen, $C_{1-6}$-alkyl, phenyl, $NH_2$, $NH(C_{1-6}$-alkyl), $N(C_{1-6}$-alkyl$)_2$, OH, O-phenyl and O—$C_{1-6}$-alkyl.

Here, the term "$C_{1-6}$-alkyl" refers to a saturated aliphatic acyclic hydrocarbon radical which can be branched or unbranched and has from 1 to 6 carbon atoms. Examples are methyl, ethyl, n-propyl, i-propyl, n-butyl, i-butyl, t-butyl, n-pentyl, i-pentyl, n-hexyl, i-hexyl.

The metal organic framework which is used in the process of the invention is known from the prior art or can be prepared by known methods. Here, the framework can be prepared by wet-chemical precipitation from conventional salts, alkoxides or metal-organic precursors or by an electrochemical route. In this case, the metal corresponding to the at least one metal ion is made available as anode material. Processes for the electrochemical preparation of such metal organic frameworks are described, for example, in WO-A 2007/131955.

The metal organic framework according to the present invention comprise pores, in particular micropores and/or mesopores. Micropores are defined as pores having a diameter of 2 nm or less and mesopores are defined by a diameter in the range from 2 to 50 nm, in each case corresponding to the definition given in Pure Applied Chem. 57, (1985), 603-619, in particular on page 606. The presence of micropores and/or mesopores can be checked by means of sorption measurements, with these measurements determining the uptake capacity of the MOF for nitrogen at 77 kelvin in accordance with DIN 66131 and/or DIN 66134.

The specific surface area, calculated according to the Langmuir model in accordance with DIN 66135 (DIN 66131, 66134), of a framework in powder form is preferably more than 300 $m^2/g$, more preferably more than 500 $m^2/g$, even more preferably more than 600 $m^2/g$, even more preferably more than 1000 $m^2/g$ and particularly preferably more than 1500 $m^2/g$.

As a shaped body, the metal organic framework according to the invention preferably has a specific surface area of at least 50 $m^2/g$, more preferably at least 100 $m^2/g$, even more preferably at least 300 $m^2/g$, even more preferably at least 750 $m^2/g$ and in particular at least 1000 $m^2/g$.

The metal or metals are elements of groups 2 to 15 of the Periodic Table of the Elements. For the purposes of the present invention, preferred metal ions are selected from the group of metals consisting of copper, iron, aluminum, zinc, magnesium, zirconium, titanium, vanadium, molybdenum, tungsten, indium, calcium, strontium, cobalt, nickel, platinum, rhodium, ruthenium, palladium, scandium, yttrium, a lanthanide, manganese and rhenium. Even greater preference is given to iron, copper, zinc, nickel and cobalt. Particular preference is given to zinc.

Lanthanides comprise La, Ce, Pr, Nd, Pm, Sm, Eu, Gd, Tb, Dy, Ho, Er, Yb and Lu.

As metal ions which can be provided in the reaction medium by means of anodic oxidation, mention may be made, in particular, of $Cu^{2+}$, $Cu^+$, $Ni^{2+}$, $Ni^+$, $Fe^{3+}$, $Fe^{2+}$, $Co^{3+}$, $Co^{2+}$, $Zn^{2+}$, $Mn^{3+}$, $Mn^{2+}$, $Al^{3+}$, $Mg^{2+}$, $Sc^{3+}$, $Y^{3+}$, $Ln^{3+}$, $Re^{3+}$, $V^{3+}$, $In^{3+}$, $Ca^{2+}$, $Sr^{2+}$, $Pt^{2+}$, $TiO^{2+}$, $Ti^{4+}$, $ZrO^{2+}$, $Zr^{4+}$, $Ru^{3+}$, $Ru^{2+}$, $Mo^{3+}$, $W^{3+}$, $Rh^{2+}$, $Rh^+$, $Pd^{2+}$ and $Pd^+$. Particular preference is given to $Zn^{2+}$, $Cu^{2+}$, $Cu^+$, $Fe^{2+}$, $Fe^{3+}$, $Ni^{2+}$, $Ni^+$, $Co^{3+}$ and $Co^{2+}$. Very particular preference is given to $Zn^{2+}$.

Examples of very particularly useful metal organic frameworks according to the present invention are Zn 2-methylimidazolate and Zn 2-ethylimidazolate. Zn 2-methylimidazolate is especially suitable.

The metal organic frameworks are generally used as shaped bodies, for example as irregular beds of spheres, rings, extrudates or pellets or as ordered internals such as packings, honeycomb bodies and monoliths.

The production of shaped bodies is described, for example, in WO-A 03/102 000. Preference is given to using beds of shaped bodies which are very densely packed. The shaped bodies therefore preferably have a diameter at their narrowest point of not more than 3 mm, more preferably not more than 2 mm, very particularly preferably not more than 1.5 mm. Very particular preference is given to shaped bodies in pellet form. An alternative is an internal in the form of a monolithic structure, since good flow likewise occurs through the large channels here while the material in the walls is likewise very densely packed.

The adsorbent is typically present in an adsorber. Apart from the metal organic framework used according to the invention, the adsorbent or the adsorber can comprise further adsorptive materials such as molecular sieves or the like.

The adsorber reactor is preferably part of an adsorber system which comprises at least three adsorbers which operate in offset phases.

This makes it possible to carry out the liberation of propane in a pseudocontinuous fashion.

The propane is preferably liberated by changing at least one physical parameter selected from the group consisting of pressure and temperature. Preference is given to at least one pressure change being carried out.

The liberation by means of a pressure change can be carried out by reducing the pressure down to a vacuum. However, for the purposes of the present invention, a reduction in the partial pressure of propane is also sufficient to liberate the latter.

This can be effected, for example, by displacement of the propane with inert gas which can easily be separated off again later.

The contacting according to the process of the invention represents an adsorption stage and a desorption stage can be carried for isolating the propane. If the adsorption and the desorption are carried out with alternate changes of pressure and/or temperature, numerous possibilities for implementing this industrially are known to those skilled in the art.

In all these methods, at least two, preferably three, particularly preferably at least four, adsorbers are operated in parallel and of these at least two of these but preferably all of these operate with a phase offset from the other adsorbers. Possible variants are a) a pressure-swing adsorption (PSA), b) a vacuum pressure-swing adsorption (VPSA), c) a temperature-swing adsorption (TSA) or a combination of various processes. These processes are known in principle to those skilled in the art and can be perused in textbooks such as W. Kast, "Adsorption aus der Gasphase—Ingenieurwissenschaftliche Grundlagen und technische Verfahren", VCH Weinheim, 1988, D. M. Ruthven, S. Farooq, K. S. Knaebel, "Pressure Swing Adsorption", Wiley-VCH, New York-Chichester-Weinheim-Brisbane-Singapore-Toronto, 1994 or D. Bathen, M. Breitbach, "Adsorptionstechnik", Springer Verlag Berlin-Heidelberg, 2001, D. Basmadjian, "The Little Adsorption Book", CRC Press Boca Raton, 1996 or publications such as A. Mersmann, B. Fill, R. Hartmann, S. Maurer, Chem. Eng. Technol. 23/11 (2000) 937. The bed of an adsorber does not necessarily have to comprise only a single adsorbent but can comprise a plurality of layers of different materials. This can be utilized, for example, to sharpen the breakthrough front of the adsorbed species during the adsorption phase.

For example, a pressure-swing adsorption for the propane/propene separation can be configured as follows: four reactors operate in parallel in the following offset phases: in phase 1, one adsorber is brought to the working pressure ($p_{maximum}$)

by introduction of fresh gas, gas from a second adsorber in the adsorption mode or offgas from a second adsorber which is at the same time decompressed. In phase 2, the adsorbent is loaded fully with propane by further introduction of feed, preferably until the entire adsorption front has broken through and no more propane is adsorbed. In this case, a second reactor is preferably connected downstream in the adsorption mode before breakthrough of the propane front. In phase 3, the adsorber is flushed with propane. Flushing can be carried out in cocurrent or countercurrent, with cocurrent being preferred. Flushing can be carried out at the adsorption pressure. Furthermore, a prior lowering of the adsorber pressure is preferred, and particular preference is given to a propane partial pressure similar to that in the adsorption phase (phase 2) and flushing phase (phase 3). The gas mixture liberated during this lowering of the pressure can be fed to another adsorber during phase 1 for building up the pressure. In phase 4, the laden and flushed adsorber is decompressed. The product is preferably discharged in countercurrent.

In addition, a subatmospheric pressure can be applied in phase 4. This embodiment is an example of a VPSA process.

To compensate for the temperature effects caused by the heat of adsorption/cold of desorption, the introduction or removal of heat can be advantageous. The introduction of heat can be carried out in various ways: conductively via internal heat exchangers, convectively via external heat exchangers or by means of radiation, for example by irradiation with microwaves or radio waves. Likewise, a heat input going beyond compensation for the cold of desorption can be utilized for additionally aiding the desorption during phase 4. Such a process represents a combination of a pressure-swing adsorption and a temperature-swing adsorption.

The desorption can also be carried out by means of displacement by an auxiliary component, for example $N_2$, $CO_2$ or steam. This exploits the fact that the auxiliary component reduces the partial pressure of propane in the gas phase while the absolute pressure can remain constant. In addition, a more strongly adsorbed auxiliary component, for example steam or $CO_2$, can also lead to displacement from the surface of the adsorbent. However, in the latter case the auxiliary component has to be removed again from the surface of the adsorbent in a further step, e.g. by increasing the temperature.

The phases do not necessarily have to have the same duration, so that a smaller or larger number of adsorbers can also be used for synchronization.

The adsorption is generally carried out at a temperature in the range from −20 to 150° C., preferably from 0 to 100° C. and particularly preferably from 10 to 60° C.

The adsorption is preferably carried out at a pressure of generally from 2 to 30 bar, more preferably from 2 to 5.5 bar. Greater preference is given to from 12 to 25 bar and very particular preference is given to from 19 to 21 bar.

The desorption phase itself can be effected either by lowering the pressure or introducing heat or by means of a combination of the two measures. The pressure is preferably reduced to a pressure of below 2.5 bar, in particular below 2 bar.

The pressure values indicated are absolute values.

The adsorption/desorption can be configured as a fixed-bed, fluidized-bed or moving-bed process. Suitable apparatuses are, for example, fixed-bed reactors, rotary adsorbers or slatted filters. A comprehensive description of possible apparatuses may be found in: Werner Kast, "Adsorption aus der Gasphase", VCH (Weinheim); H. Brauer, "Die Adsorptionstechnik ein Gebiet mit Zukunft", Chem.-Ing. Tech 57 (1985) 8, 650-653; Dieter Bathen, Marc Breitbach "Adsorptionstechnik", VDI-Buch, 2001.

To desorb the gases adsorbed on the adsorbent, the latter is heated and/or depressurized to a lower pressure.

The liberated propene obtained from the process of the invention for the industrial isolation of propene can preferably be obtained in a purity of over 80% by volume, based on the sum of the proportions by volume of propane and propene. The purity is more preferably greater than 90% by volume, more preferably at least 95% by volume, in particular at least 98.5% by volume.

The present invention further provides for the use of a porous metal organic framework comprising at least one at least bidentate organic compound coordinated to at least one metal ion for the industrial isolation of propene from a gas stream comprising at least propene and propane by at least partial removal of propane from the gas stream, wherein the at least bidentate organic compound is an imidazolate which is unsubstituted or has one or more substituents selected independently from the group consisting of halogen, $C_{1-6}$-alkyl, phenyl, $NH_2$, $NH(C_{1-6}$-alkyl), $N(C_{1-6}$-alkyl$)_2$, OH, O-phenyl and O—$C_{1-6}$-alkyl.

EXAMPLES

Example 1

Electrochemical Preparation of the Inventive Adsorbent Zn(II) 2-methylimidazolate (Zn(MIM)$_2$)

The electrolyte comprising 76.1 g of 2-methylimidazole, 85.8 g of methyltributylammonium methylsulfate (MTBS), 1810 g of methanol and 750.2 g of water is introduced into a cell circuit. A conductivity of 4.8 mS/cm is measured.

The cell circuit comprises a tubular cell, a glass cooler and a circulating pump. The pump circulates the electrolyte or the resulting suspension at about 600 l/h.

The tubular cell comprises a stainless steel tube (length: 55 cm, internal diameter: 5 cm) as cathode and a zinc rod as anode (length: 55 cm, diameter: 1.94 cm, surface area: 3.41 cm$^2$). The arrangement in the electrolysis cell ensures, by means of various airtight seals and screw connections, that the electrodes are arranged concentrically and guarantee a circumferentially homogeneous gap between cathode and anode through which the electrolyte thermostatted to 29° C. is pumped.

At a current density of 5.1 A and a cell voltage of from 4.6 to 5 V, the cell is operated for 4.8 hours until a quantity of electricity of 1 faraday per mole of 2-methylimidazole has been transferred (24.6 Ah). During the experiment, the cell is flushed with a stream of inert gas to remove hydrogen formed and prevent formation of an explosive $H_2$ mixture.

After the electrolysis is complete, the electrolyte is filtered and washed with 300 g of methanol. The weight of the zinc anode is reduced by 29.0 g. The crystalline product is dried at 80° C. and 1 mbar, giving 100.9 g of Zn(MIM)$_2$ (yield 98%). The surface is determined by the Langmuir method in accordance with DIN 66135 and is 1718 m$^2$/g.

Example 2

Separation of Propane from a Propane/Propene-Comprising Mixture

The material from Example 1 is mixed with 3% by weight of graphite and shaped to produce 1.9×1.9 mm pellets (surface area: 1266 m$^2$/g) and crushed to give crushed material (0.5-1 mm). An adsorber reactor (diameter: about 2.5 cm) is charged with 50 g of the material. Before the experiment, the bed is flushed with dry nitrogen at 130° C. for more than 16 hours. A pressure of 7.5 bar is subsequently built up at 25° C. using pure He and, under these conditions, a mixture of 5% of propane and 5% of propene in helium is fed into the reactor. The composition of the exiting gas is monitored on-line by means of infrared spectrometry (IR). The course of the IR signal for the exiting gas (concentration C in %) is shown as function of the time t in min. in FIG. 1. Initially, both components are adsorbed on the surface, so that neither of the components is detected in the IR cell. After some time, the propene component (black symbols) breaks through first, which is detected by means of the increase in this signal in the infrared cell. However, the propane continues to be adsorbed for some time and breaks through only at a later point in time (white symbols).

Comparative Example 3

Separation of a Propane/Propene Mixture on a 13X Molecular Sieve

Figure 2:
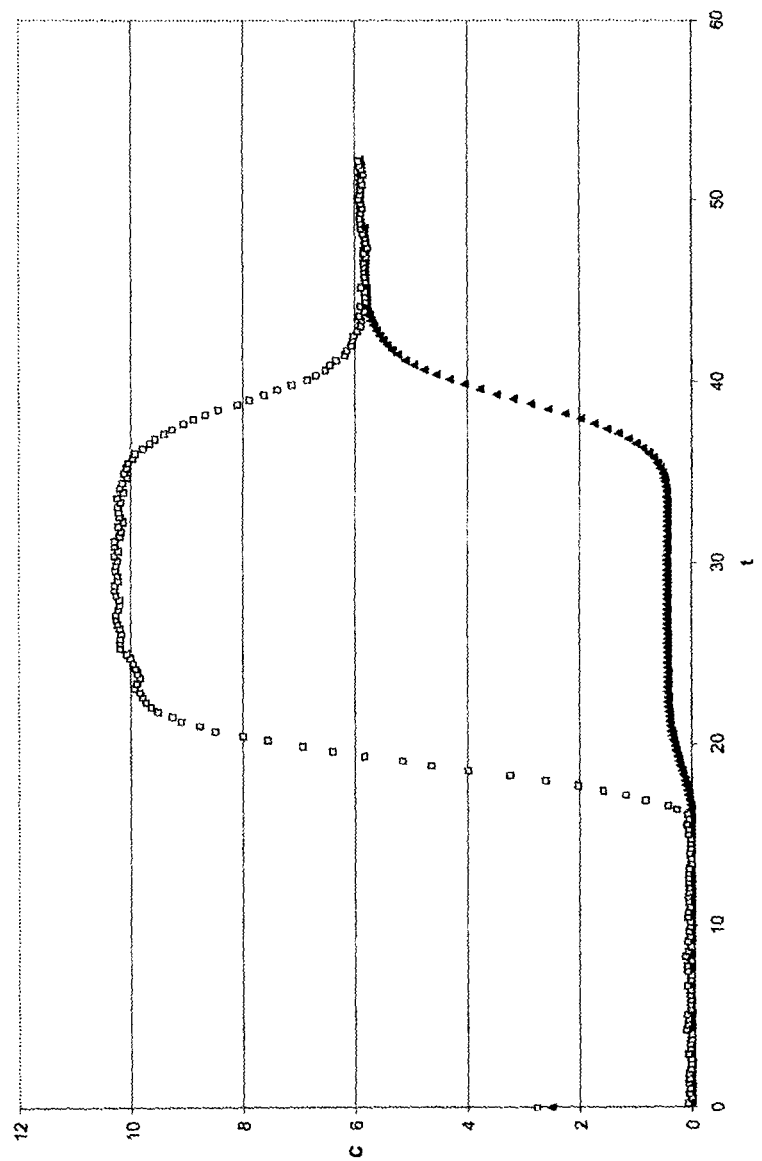

For comparison, the reactor is charged with 50 g of a "molecular sieve 5A" (from Carl Roth GmbH+Co. KG, Schoemperlenstr. 3-5, Karlsruhe, Germany). The molecular sieve is predried beforehand at 180° C. in a vacuum drying oven for 10 hours. The experiment is carried out in a manner analogous to Example 2. The result is shown in FIG. 2 (propene: black symbols, propane: white symbols), where C and t have the same meanings as in FIG. 1. In this case, propane breaks through first while propene continues to be adsorbed and breaks through only at a later point in time after complete saturation of the sorbent.

The invention claimed is:

1. A process for industrial isolation of propene from a gas stream comprising at least propene and propane, the process comprising:
    contacting the gas stream with an adsorbent comprising a porous metal organic framework comprising at least one at least bidentate organic compound coordinated to at least one metal ion, with the adsorbent becoming laden with propane and the gas stream therefore having an increased proportion of propene,
    wherein the at least bidentate organic compound is an imidazolate which is unsubstituted or has at least one substituent independently selected from the group consisting of a halogen, a $C_{1-6}$-alkyl, a phenyl, $NH_2$, an $NH(C_{1-6}$-alkyl), an $N(C_{1-6}$-alkyl)$_2$, an OH, O-phenyl, and an O—$C_{1-6}$-alkyl.

2. The process according to claim 1, wherein the gas stream comprises from 20% by volume to 80% by volume of propene based on a sum of proportions by volume of propene and propane.

3. The process according to claim 1, wherein the gas stream is an optionally purified product stream from a preparation of propene.

4. The process according to claim 3, wherein the optionally purified product stream originates from at least one selected from the group consisting of a cracking process, a dehydrogenation of propane, an olefin transformation, and a methanol/dimethyl ether transformation for a preparation of propene.

5. The process according to claim 4, wherein the optionally purified product stream originates from a dehydrogenation of propane to prepare propene.

6. The process according to any of claim 1, wherein the gas stream has a propene content, after the contacting, of over 80% by volume based on a sum of proportions by volume of propene and propane.

7. The process according to any of claim 1, wherein at least one of (a) and (b), is fulfilled:
    (a) the contacting is carried out at a temperature in a range from −20° C. to 150° C.;
    (b) the contacting is carried out at a pressure in a range from 2 bar, absolute, to 30 bar, absolute.

8. The process according to any of claim 1, wherein the at least one metal ion is selected from the group consisting of a copper ion, an iron ion, an aluminum ion, a zinc ion, a magnesium ion, a zirconium ion, a titanium ion, a vanadium ion, a molybdenum ion, a tungsten ion, an indium ion, a calcium ion, a strontium ion, a cobalt ion, a nickel ion, a platinum ion, a rhodium ion, a ruthenium ion, a palladium ion, a scandium ion, a yttrium ion, a lanthanide ion, a manganese ion and a rhenium ion.

9. The process according to any of claim 1, wherein the imidazolate has at least one $C_{1-6}$-alkyl substituent.

10. The process according to claim 2, wherein the gas stream is an optionally purified product stream from a preparation of propene.

11. The process according to claim 10, wherein the optionally purified product stream originates from at least one selected from the group consisting of a cracking process, a dehydrogenation of propane, an olefin transformation, and a methanol/dimethyl ether transformation for a preparation of propene.

12. The process according to claim 11, wherein the optionally purified product stream originates from a dehydrogenation of propane to prepare propene.

13. The process according to claim 2, wherein the gas stream has a propene content, after the contacting, of over 80% by volume based on a sum of proportions by volume of propene and propane.

14. The process according to claim 3, wherein the gas stream has a propene content, after the contacting, of over 80% by volume based on a sum of proportions by volume of propene and propane.

15. The process according to claim 10, wherein the gas stream has a propene content, after the contacting, of over 80% by volume based on a sum of proportions by volume of propene and propane.

16. The process according to claim 4, wherein the gas stream has a propene content, after the contacting, of over 80% by volume based on a sum of proportions by volume of propene and propane.

17. The process according to claim 11, wherein the gas stream has a propene content, after the contacting, of over 80% by volume based on a sum of proportions by volume of propene and propane.

18. The process according to claim 5, wherein the gas stream has a propene content, after the contacting, of over 80% by volume based on a sum of proportions by volume of propene and propane.

19. The process according to claim 12, wherein the gas stream has a propene content, after the contacting, of over 80% by volume based on a sum of proportions by volume of propene and propane.

20. The process according to claim 2, wherein at least one of (a) and (b), is fulfilled:
    (a) the contacting is carried out at a temperature in a range from −20° C. to 150° C.;
    (b) the contacting is carried out at a pressure in a range from 2 bar absolute to 30 bar absolute.

* * * * *